United States Patent
Neumann et al.

(10) Patent No.: US 8,911,817 B2
(45) Date of Patent: Dec. 16, 2014

(54) METHOD AND DEVICE FOR COATING CATHETERS OR BALLOON CATHETERS

(75) Inventors: Hans-Georg Neumann, Rostock (DE); Mischa Buhrmeister, Papendorf (DE)

(73) Assignee: DOT GmbH, Rostock (DE)

( * ) Notice: Subject to any disclaimer, the term of this patent is extended or adjusted under 35 U.S.C. 154(b) by 239 days.

(21) Appl. No.: 13/379,323

(22) PCT Filed: Jun. 16, 2010

(86) PCT No.: PCT/EP2010/058493
§ 371 (c)(1),
(2), (4) Date: Dec. 19, 2011

(87) PCT Pub. No.: WO2010/146096
PCT Pub. Date: Dec. 23, 2010

(65) Prior Publication Data
US 2012/0100279 A1  Apr. 26, 2012

(30) Foreign Application Priority Data

Jun. 17, 2009 (DE) .......... 10 2009 025 638

(51) Int. Cl.
| | |
|---|---|
| A61M 25/10 | (2013.01) |
| B05D 3/02 | (2006.01) |
| B05C 3/02 | (2006.01) |
| B05C 11/00 | (2006.01) |
| B05D 7/20 | (2006.01) |
| B05C 3/09 | (2006.01) |
| B05C 5/02 | (2006.01) |
| B05D 7/00 | (2006.01) |

(52) U.S. Cl.
CPC ... *B05D 7/20* (2013.01); *B05C 3/09* (2013.01); *B05C 5/0241* (2013.01); *B05D 7/00* (2013.01)
USPC ...... 427/2.28; 427/2.24; 427/379; 427/372.2; 118/58; 118/62; 118/410; 118/419; 118/421

(58) Field of Classification Search
CPC .......... B05D 7/00; B05C 3/10; B05C 5/0241; B05C 11/06
USPC .......... 427/2.28, 2.24, 2.1, 430.1, 379, 372.2; 118/410, 419, 420, 421, 423, 404, 405, 118/58, 62, 63
See application file for complete search history.

(56) References Cited

U.S. PATENT DOCUMENTS

| | | |
|---|---|---|
| 5,102,402 A | 4/1992 | Dror et al. |
| 6,254,921 B1 * | 7/2001 | Chappa et al. ................ 427/2.3 |

(Continued)

FOREIGN PATENT DOCUMENTS

| | | |
|---|---|---|
| DE | 10 2007 010 354 | 4/2008 |
| DE | 10 2007 036 685 | 2/2009 |

(Continued)

*Primary Examiner* — Cachet Sellman
(74) *Attorney, Agent, or Firm* — McNees Wallace & Nurick LLC

(57) ABSTRACT

A method and apparatus for coating catheters or balloon catheters is disclosed in which the catheter or balloon catheter is radially surrounded completely or almost completely at a constant distance by a device that applies a coating solution so that the coating solution completely fills the space between the catheter or balloon catheter and the device and thus completely surrounds the catheter or balloon catheter, relative motion is effected between the device and the catheter or balloon catheter in the axial direction across the surface of the catheter or balloon catheter multiple times, and partial drying of the applied coating solution occurs between the individual coating stages.

17 Claims, 1 Drawing Sheet

(56) References Cited

U.S. PATENT DOCUMENTS

| | | |
|---|---|---|
| 6,322,847 B1 | 11/2001 | Zhong et al. |
| 6,329,444 B1 * | 12/2001 | McGlothlin et al. .......... 523/105 |
| 6,406,754 B2 | 6/2002 | Chappa et al. |
| 7,381,273 B2 * | 6/2008 | Collins .................. 118/642 |
| 2003/0100830 A1 * | 5/2003 | Zhong et al. ................ 600/431 |
| 2004/0071861 A1 | 4/2004 | Mandrusov et al. |
| 2005/0196518 A1 * | 9/2005 | Stenzel ........................ 427/2.1 |
| 2006/0029720 A1 | 2/2006 | Panos et al. |
| 2007/0128343 A1 | 6/2007 | Chappa |
| 2007/0222132 A1 * | 9/2007 | Anderson et al. .............. 269/37 |
| 2010/0228342 A1 * | 9/2010 | Thornton et al. ............ 623/1.42 |
| 2011/0238011 A1 | 9/2011 | Scheller et al. |

FOREIGN PATENT DOCUMENTS

| | | |
|---|---|---|
| EP | 0 519 063 | 12/1992 |
| WO | WO-00/45744 | 8/2000 |
| WO | WO-02/076509 | 10/2002 |
| WO | WO-2004/006976 | 1/2004 |
| WO | WO-2007/090385 | 8/2007 |
| WO | WO-2008/086794 | 7/2008 |

* cited by examiner

METHOD AND DEVICE FOR COATING CATHETERS OR BALLOON CATHETERS

BACKGROUND OF THE INVENTION

The invention relates to a method and a apparatus for the targeted coating process of catheters or balloon catheters. The term "catheters" herein means catheters exclusive of a balloon.

The treatment of stenosises is provided by placing stents and/or by using so called balloon catheters in order to dilate the respective vessels again. Here, in recent years considerable results have been achieved. Because of that, in many cases a dilatation of the vessel lumen exceeding 90% of the value before the constriction has started can be achieved.

However, in the past a renewed constriction (restenosis) has happened with numerous patients after a few months. Mostly, this is a consequence of the immoderate proliferation, especially of the smooth muscle cells, due to the forcible dilatation of the vessel walls. After healing up the injury the proliferation thereof does not stop immediately, thus frequently leading to a restenosis. One can inhibit this effect by coating the stents and the balloon catheters with an anti-restenosis active agent.

As a rule, the balloon catheters and stents have to travel a long path inside the vessels until they reach the location of the vessel constriction. Here, one is faced with the problem to prevent a premature separation of the active agents prior to reaching the destination and to ensure that the active agent is available in a predefined quantity at the location of the vessel constriction.

With the exclusive application of balloon catheters the contact time with the vessel wall only lasts some seconds to a few minutes during the dilatation of the balloon which aggravates the situation. Thus, it is necessary for the existing contact area to completely be used if possible by means of a uniform coating process, and for the active agents to be provided with a high bio-availability.

The stenosis of arteries is often combined with massive calcification. The vessels concerned can only be dilated to their original lumen again by means of very high pressure. For this purpose, a pressure-resistant balloon is inserted which forms into a stable cylinder through dilatation closely bearing against the vessel wall and pressing the active agents applied from the outside with appropriately high pressure against the vessel walls.

With the same method a local medicament dose can also be carried out without a dilatation of the vessels being necessary. Examples can be found with alterations of the vessel wall which are not associated with stenosis (e.g. vulnerable plaques, deposited thrombi). Other examples include the treatment of vessels by mechanical means or by thermal methods. In these cases, an overstretching of the vessel walls and a laceration combined therewith are not desired. As a result, the balloons which are used do not either bear against the irregular vessel walls completely and the active agents will be pressed against these with lower pressure.

In numerous publications there are proposed solutions which should prevent the premature separation of the active agents with the stents. One possibility consists in housing the active agent in small cavities and by preventing the premature separation by means of a protective coating (US 2004/0071861 A, WO 2003/035131 A). Likewise, described is the possibility to apply an inflexible final coating over the active agent layer which breaks open with the expansion (WO 2000/45744 A1). By contrast, DE 102007010354 A1 describes a combination of the active agent layer and absorbable sacrificial coating layer situated thereabove.

Coatings with active agents have also been described with balloon catheters. However, due to the greater surface and the folded structure they are more difficult to implement. Beyond that, an immediate release of the active agents from the catheter to the vessel walls is necessary as a result of the short contact time.

The possibility of reliably preventing restenosis even during the short contact of the balloon catheters with the blood vessels has been disclosed for the first time in WO 2002/076509 A2. Therein a balloon catheter is described which releases the active agent immediately in a bio-available form during contact with the vessel wall.

In numerous publications of the prior art there are described active agents and complex combinations from very diverse materials which are suitable for coating stents and/or balloon catheters.

In EP 0519063 B1 there is disclosed the possibility to coat a folded balloon being initially expanded and then deflated again with micro capsules in which a pharmaceutical agent can be included. A disadvantage of this embodiment lies in the fact that the majority of the micro capsules is separated from the balloon surface while inserting the balloon catheter into a vessel, and that only the capsules in the folds reach the destination. Thus, the quantity of the micro capsules being available during the expansion and hence the separated agent quantity is not known.

WO 2007/090385 A2 discloses a possibility of providing the folds of a balloon catheter specifically with an agent. With this embodiment the entire agent stock reaches the destination.

In the aforementioned two embodiments (EP 0519063 B1 and WO 2007/090385 A2) the agent is only transferred via one part of the balloon surface to the vessel walls. In this manner, it cannot be made certain that the agent in necessary quantity does reach all affected places of the vessel wall.

In WO 2004/006976 A, lipophilic pharmaceutical preparations are applied onto a structured, especially rough, surface of the expanded balloon through spraying, immersion or absorbing. By means of a lipophilic layer between the pharmaceutical preparation and the balloon surface the separation of the agent should be facilitated.

The most often described solutions for coating catheters and balloon catheters are based on a substrate decelerating the release of the agents. However, in the course of this the contact time between the balloon surface and ambient tissue is relatively short.

In contrast to this, DE 102007036685 A1 discloses the coating process of a balloon catheter in such a manner that at least one agent is immediately released. very diverse compositions functioning as agents and transport mediators are disclosed therein.

In WO 2008/086794 A2 there is generally disclosed the coating process of catheter balloons by means of a volumeter and a dispensing device. Thereby a great many different methods for the coating process are used. However, it is known that not all methods described therein result in a surface having the same characteristics in quality.

In U.S. Pat. No. 6,322,847 B1 there is disclosed a possibility of removing surplus portions resulting from the coating process by means of a gas jet. But it is more useful to avoid such surplus portions already during the coating process, and thus to render superfluous a later treatment. Drying the coating during the treatment with the gas jet cannot completely be avoided. Consequently, the calibration of the system is very expensive because, on the one hand, a gas jet which is too weak cannot remove the surplus portions of the layer which have become more solid, and, on the other hand, a gas jet which is too strong can damage the layer in such a manner that the object to be coated is not completely covered any longer.

US 2006/0029720 A1 discloses a method of coating a medical device by applying the coating solution onto the top end of the vertically set up medical device. Then, the distribution takes place by means of flow processes due to gravity. One advantage of the invention is the good possibility of automation. With medical devices, in particular stents, uniform coating and, in particular, a very uniform distribution of the contained agents across the surface is of great significance. However, uniform distribution of the coating solution represents a problem with this method. This particularly applies to heavily structured objects such as stents or balloon catheters. The formation of projections and drops cannot practically be avoided with the flow technique, and additional methods, such as e.g. according to U.S. Pat. No. 6,322,847 B1, have to be used.

U.S. Pat. No. 6,406,754 B2 and U.S. Pat. No. 6,254,921 B1 describe a device and a method for coating a tubular or wirelike medical device including the possibility to leave out such regions which should not obtain any coating. With this method it is also possible to apply various coatings onto different regions of the medical device. For this purpose, a chamber is used which encloses the medical device at the ends such that coating solution is not allowed to escape. As a result, coating can take place through feeding and draining off the coating solution in the chamber or by means of a relative motion of the chamber and medical device. This approach has just several disadvantages. The impermeable seal of the chamber at the ends is technologically very expensive because many of these products are either heavily structured, e.g. stents, or have folds of such as e.g. balloon catheters. During a relative motion of the chamber and medical device the new coating, already existing coatings or even the medical device itself can be damaged the impermeable seal. Likewise, residual quantities remaining in the chamber and damages of the coating at the sealing positions represent a problem during opening the chamber.

In US 2007/0128343 A1 there is disclosed a possibility of having two spray nozzles by means of which two different coating solutions can be applied. A spraying method has several disadvantages which are not overcome by the present publication. For a uniform coating it is necessary to move the spray nozzles and the object to be coated relative to the longitudinal axis and to carry out a rotational motion of the object or an adequate motion of the spray nozzles as well. The well-defined quantity of the substances applied on the objects is just hard to guarantee as always a part of the substances do not arrive on the object to be coated during spraying. However, this is of great significance exactly with medically effective components.

Practicable compositions of coating solutions are described in detail in the prior art documents. The methods for coating are primarily presented in terms of calculated filling of the folds of the catheter balloon and/or applying a specific quantity of the coating solution.

The same way, there are disclosed many possibilities of designing the surface of the balloon, be that through structuring or by means of an additional treatment.

Common to prior art documents is that the effect of the coating method on the structure and the quality of the surface is not sufficiently taken into account. Likewise, the ambient conditions and further process parameters having a decisive influence on the quality properties of the surfaces are only insufficiently represented.

SUMMARY OF THE INVENTION

It is an object of the invention to develop a method and an apparatus which enable a continuous and uniform coating of catheters and balloon catheters. At that commercially available catheters without any necessary special pre-treatment are used.

The method for coating catheters or balloon catheters according to the invention is characterized in that
a. the catheter is radially enclosed completely or almost completely at a constant distance by a device that contains a measured quantity of a coating solution in such a way:
b. that the coating solution completely fills the space between the catheter and the device and thus completely radially surrounds the catheter on a partial axial section;
c. that the device is repeatedly moved in the axial direction across the surface of the catheter; and
d. that specific partial drying of the applied coating solution occurs between the individual coating processes.

Following complete drying takes place according to the prior art.

Further, a gas flow can be generated by means of an apparatus for generating a gas flow opposite to the flow direction of the coating solution which prevents the enrichment of the coating solution and/or the formation of drops, e.g. at the end points of the catheter. This step is particularly advantageous to use with balloon catheters at the ends of the balloon.

The gas flow consists of a gas or gas mixture, occurs uniformly or with time variations in direction and intensity, and can thermally be affected time-variably.

Both partial drying of the coating between the coating processes and final drying of the coating can be supported by an additional second airstream. The extent of drying can be set in a specific time unit via the temperature and intensity of the airstream, and thus can be matched with the period of a coating process.

Alternatively the drying process can also be supported by variation of the pressure. In particular, conducting partial drying or final complete drying in a chamber under reduced (sub-atmospheric) pressure will accelerate the drying process. Likewise, other methods common to those skilled in the art are applicable.

The coating process of the catheter including the partial drying and complete drying can be repeated several times. In the course of this a change of the coating solution is possible.

In another embodiment the axial motion is generated by the motion of the catheter, by the motion of the enclosing device or by the motion of both. The catheter is stationary or will be rotated about its longitudinal axis.

The coating solution contains at least one pharmacological agent, optionally none, one or several additives, and at least one solvent in a defined composition. It will be renewed in a continuously or discontinuously defined manner.

When coating a balloon catheter, it partially deploys by warming-up prior to and/or during the coating process. Warming-up occurs uniformly with a spatial distribution and/or a time variation by heating the ambient, by heating the holding device, by means of radiation heat or through a heated gas stream across the balloon catheter. Because of this partial deployment the coating solution also reaches on the inside of the folds, and with the application of the balloon catheter an agent included in the coating solution is allowed to have its particular effect on the entire surface contacted by the balloon catheter.

The apparatus according to the invention radially encloses the catheter completely or partially in such a manner that between the catheter and the apparatus a space of constant radial dimension is created which dimension is great enough to reliably prevent contact between the surface of the catheter and the apparatus, but sufficiently small that a minimally required quantity of the coating solution fills that space. In the axial direction, this extension of the device for coating is relatively small with respect to the length of the object to be coated.

The enclosing device is constructed as a ring, tube or spiral. It can comprise a narrow slot and consists of metallic and/or non-metallic materials. The top surface of the enclosing device is coated and/or provided with an additional structure.

The catheter is fixed in a holding device by means of a support upon which the catheter is pushed. This device is repeatedly moved axially across the catheter. At the ends of the catheter gas flows are generated which prevent accumulations of the coating solution and/or the formation of drops at the ends of the catheter. A heated gas stream supports partial drying between the coating processes and supports final drying.

The method according to the invention is not only suitable for coating catheters and balloon catheters but also for coating all other catheters and other preferably cylindrical medical instruments having relatively invariable diameter.

Preferably, the coating solution contained in the apparatus is completely consumed during the coating process which can comprise multiple coating and drying processes. Since with multiple consecutive coating processes wetting the device with the coating solution at the outset of the coating process is equivalent to wetting at the end of coating process, the obtained coating can very precisely be determined from the quantity of the consumed coating solution. This is not the case with dipping and spraying processes known from the prior art. For a greater layer thickness the device can newly be filled as well with an exactly metered quantity of coating solution during the coating process.

Through partial drying of the coating solution between the individual coating processes it is achieved that the coating already being present is not pushed together or damaged during the next process. Because of that a very uniform coating is achieved with a layer thickness being selectable in wide ranges as being not possible with other methods (e.g. US 2006/0029720 A1). Later removal of excess coating solution (e.g. U.S. Pat. No. 6,322,847 B1) is not necessary.

By means of the rate of partial drying between the coating processes it can be set whether the layers from the individual coating processes are combined to a single layer again (lower rate of drying) or whether the single layers remain maintained in the cross-section as far as possible.

A repetition of the whole process in the same way is possible with a different coating solution as well. Then, it depends on the coating solutions used and on the total layer desired whether partial drying or complete drying is advantageous in the mean time.

The invention will be explained in more detail on the basis of drawings.

DETAILED DESCRIPTION OF THE INVENTION

Figure 1:
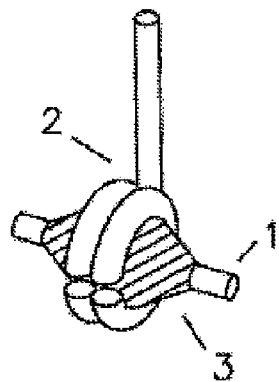
FIG. 1 shows apparatus according to the invention with a coating device which does not completely enclose the catheter.
Figure 2:
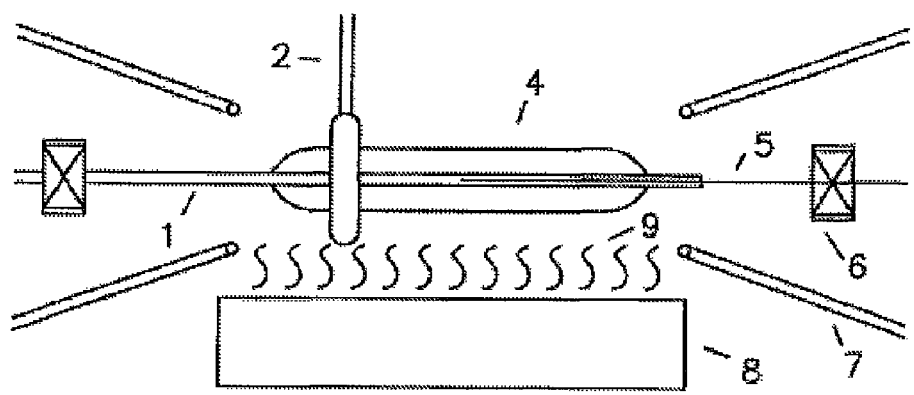
FIG. 2 shows apparatus according to the invention with the holding device and means for the generation of a gas flow.

The device 2 for coating a catheter according to FIG. 1 radially encloses catheter 1 either completely or partially. Herein, is shown partial surrounding of catheter 1. There is a distance between catheter 1 and device 2 such that the inner radial dimensions of device 2 are greater than e.g. the diameter of a folded balloon. Device 2 may have different embodiments such as a ring, a tube, a spiral or another appropriate shape. Device 2 can consist of metallic or non-metallic materials. With respect to the axial dimension of the catheter balloon the width of device 2 measured parallel to the axis of the catheter balloon is small. (FIG. 2).

The surface of enclosing device 2, in particular of the inside, can be coated and/or provided with an additional structure.

Into enclosing device 2 there will be filled a defined quantity of coating solution 3 which will be renewed by a defined quantity as well during the coating process. The renewal can take place in a continuous or discontinuous manner. The coating solution 3 contains at least one pharmacological agent, optionally one or more additives, and at least one solvent in a predetermined composition.

The coating solution 3 encloses catheter 1 completely radially in accordance with the dimensions of enclosing device 2, and is moved in the axial direction across the surface of catheter 1 wherein a defined quantity of coating solution 3 will be applied. The axial motion is generated in two ways: either catheter 1 moves through enclosing device 2 or enclosing device 2 is moved across catheter 1. Another possibility is that both, catheter 1 and enclosing device 2, are moved. Also, catheter 1 can be rotated about its longitudinal axis or can be stationary.

Partial drying takes place right during the coating process. This process can be accelerated by heating. In the example, partial drying between the coating processes is accelerated by heated air 9, which escapes from a fan 8 or from another appropriate device.

The enclosing device 2 can be moved several times across catheter 1 wherein the balloon of the balloon catheter will completely be provided with a layer. By repeated surface drying and moistening of the layer any damage to the layer before the process is completed will be eliminated during the next operation, and a very homogeneous uniform layer, on the other hand, will be formed at the end of the coating process.

In one embodiment, catheter 1 is a balloon catheter (FIG. 2), wherein the balloon of balloon catheter 4 will be coated. Partial inflation of the folded balloon occurs by warming up. Several factors are allowed to provide warming up the balloon catheter: warming up of the ambient, warming up of the holding device 6, radiation heat, a heated gas stream across the balloon catheter or another method usable for warming up. Warming up can take place uniformly, with a spatial distribution and/or with time variation.

To ensure homogeneous coating a flowing gas is used opposite to the flowing direction of the coating solution by means of a device for the generation of a gas flow 7. The gas stream takes place uniformly or with time variations in direction and intensity.

Through device 2 the layers are generated with great regularity wherein the applied quantity of the agent can be determined in a very exactly reproducible manner.

Example 1

Coating the balloon of a balloon catheter with a pharmacological agent and a binding agent A solution will be prepared according to the prior art from a pharmacological agent, e.g. a medicine for preventing restenosises, a binding agent, e.g. shellac, and a solvent preferably a highly volatile alcohol.

The catheter 1 of the balloon catheter is formed as a tube comprising an aperture at the forward end. A thin wire 5 is inserted into this aperture. Subsequently, catheter 1 will be clamped into the coating device such that the balloon is located between the two holding devices 6.

The vicinity of the balloon will be heated with hot air 9 from a fan 8. However, any other method known from the prior art can be used to warm the balloon. The selected temperature then depends on the composition of coating solution 3. At the same time, due to heating the folds of the balloon slightly erect whereby uniform coating of the entire surface is possible.

To ensure homogeneous balloon coating one gas stream each is additionally generated from the two ends of holding device 6 in the direction of the balloon center by means of the device for the generation of a gas flow 7.

In this case, enclosing device 2 is a ring which is not completely closed such that it can be pushed over the catheter, over the wire or over the balloon (FIG. 1) while the balloon catheter is clamped. The ring will then be positioned such that the balloon is located in the center of the ring. A precisely dimensioned quantity of coating solution 3 will be added in the ring such that a uniform thin layer is forming around the balloon to be coated. The ring will uniformly be moved back and forth between the two ends of the balloon. At the same time, the whole proceeding will be supervised by a camera.

Because of the fed hot air partial drying of the coating occurs such that a renewed partial solution of the layer having begun to dry takes place with every new wetting. Thus, the damage of the already formed layer will be eliminated during the next proceeding, and a very homogeneous uniform layer is formed at the end of the coating process.

When the solution is spent, over and over again a precisely metered quantity of coating solution 3 will be added as long as the quantity of the active agent aimed at is located on the balloon surface. The quantity of coating solution 3 required to deposit the desired quantity of the active agent on the balloon surface results from the selected concentration of the active agent in coating solution 3, the surface of the balloon in the unfolded condition and the quantity of the active agent aimed at per unit area.

After the coating process the balloon will be aired for a few minutes, packed and sterilized according to the known prior art.

Example 2

Coating a balloon catheter with a hydrophilic substance

A solution will be prepared from a hydrophilic substance, e.g. shellac, and a solvent, preferably a highly volatile alcohol. The solution will be filled in the quantity being required for a coating process with a metering device according to the prior art. The required quantity of coating solution 3 results from the selected concentration of the hydrophilic substance in the solution, from the surface of the balloon and the quantity of the substance aimed at per unit area.

In this example the enclosing device 2 is a short complete tube section (FIG. 2), i.e., an endless annulus, Device 2 for coating is positioned with respect to the catheter 1 such that the latter is situated approximately in the center of the tube section. The vicinity of catheter 1 will be heated with hot air. As a result, the selected temperature depends on the composition of coating solution 3. Then, the tube section will uniformly be moved back and forth between the two ends of the balloon. At the same time, coating solution 3 will continuously be fed as long as the previously measured quantity is being spent. The whole proceeding is supervised by means of a camera.

Because of the fed hot air, fast drying occurs such that during every new wetting a renewed partial solution of the layer already having begun to dry is taking place. As a result, a highly uniform surface will be generated.

After the coating process the catheter can be aired and will subsequently be packed and sterilised according to the known prior art.

The invention claimed is:

1. A method of coating a catheter or a balloon catheter, comprising:
   a. surrounding the circumference of the catheter or balloon catheter completely or substantially with a device for applying a coating solution to the catheter or balloon catheter, the catheter or balloon catheter and the device being so arranged that there is a uniform radial space between the catheter or balloon catheter and the device;
   b. by means of the applying device filling the coating solution into the space;
   c. imparting relative axial motion to the applying device and the catheter or balloon catheter so that the catheter or balloon catheter is traversed by the applying means a plurality of times while the coating solution is fed into the space and onto the surfaces of the catheter or balloon catheter so that the coating is applied stagewise;
   d. predetermining intervals between stages so that coating applied in each stage only partially dries before the next stage; and
   e. after a final coating stage, completely drying the coating.

2. The method according to claim 1, further comprising directing gas flows to ends of the catheter or balloon catheter during application of the coating solution thereto to prevent uneven accumulations or drops of the coating solution at the ends of the catheter or balloon catheter.

3. The method according to claim 2, wherein the gas flow is fixed or variable in orientation, intensity or temperature.

4. The method according to claim 1, further comprising partial drying of each non-final stage of the coating process by application of heat and, after the final stage of the coating, drying the final coating by more intense application of heat.

5. The method according to claim 4, wherein each partial drying and complete drying is performed in a reduced pressure chamber so as to accelerate the partial drying and complete drying.

6. The method according to claim 1, further comprising repeating steps "a" through "e" at least once thereby to apply a plurality of coatings to the catheter or balloon catheter, the coatings of the plurality of coatings being visually distinguishable from each other when viewed in cross-section.

7. The method according to claim 1, further comprising initially providing a balloon catheter in a folded condition and, before or during application of the coating solution to the balloon catheter, warming the balloon catheter thereby to at least partially unfold the balloon catheter.

8. The method of claim 7, wherein the warming is effected by at least one of heating the area wherein the balloon catheter is located, heating holding devices which are holding the balloon catheter, applying radiant heat to the balloon catheter, or generating a heated gas stream and directing it across the balloon catheter.

9. The method of claim 1, wherein, while the coating solution is being applied, the catheter or balloon catheter is moved in an axial direction while the applying device is stationary in the axial direction or the catheter or balloon catheter is moved in the axial direction while the heating device is stationary in the axial direction or both the catheter or balloon catheter and the applying device are moved in the axial direction.

10. The method according to claim 1, wherein the catheter or balloon catheter is held rotationally stationary while the coating solution is being applied thereto.

11. The method according to claim 1, wherein the catheter or balloon catheter is rotated about its longitudinal axis while the coating solution is being applied.

12. The method according to claim 1, wherein the coating solution comprises a pharmacological agent and a solvent.

13. The method according to claim 12, wherein the coating solution further comprises at least one additive.

14. The method according to claim 1, further comprising replenishing a supply of the coating solution for the applying device continuously as the coating solution is applied to the catheter or balloon catheter.

15. The method according to claim 1, further comprising replenishing a supply of the coating solution for the applying device batchwise.

16. Apparatus for coating a catheter or balloon catheter, comprising a device for applying a coating solution to the catheter or balloon catheter, the applying device comprising a conduit for completely or substantially surrounding the circumference of the catheter or balloon catheter and conducting the coating solution onto the catheter or balloon catheter as a coating; support devices for supporting the catheter or balloon catheter concentrically within the applying device, the applying device and the catheter or balloon catheter being movable back and forth repeatedly relative to each other in directions of a common axis of the catheter or balloon catheter and the applying device for thereby coating the catheter or balloon catheter in stages; means for heating coating on the catheter or balloon catheter for partial or complete drying of coating applied as an initial or intermediate stage of coating or as a final stage of coating, respectively; and means for directing flows of hot gas to ends of the catheter or balloon catheter during application of the coating solution thereby to prevent formation of accumulation or drops of the coating solution at the ends of the catheter or balloon catheter.

17. The apparatus according to claim 16, wherein surfaces of the applying device for surrounding the catheter or balloon catheter are coated.

* * * * *